United States Patent [19]

Dudrick et al.

[11] Patent Number: 5,026,721

[45] Date of Patent: Jun. 25, 1991

[54] AMINO ACID NUTRITIONAL SUPPLEMENT AND REGIMEN FOR ENHANCING PHYSICAL PERFORMANCE THROUGH SOUND NUTRITION

[76] Inventors: Stanley J. Dudrick, 702 Pine St., Philadelphia, Pa. 19106; Edward J. Guinn, 23 S. Brokenfern, The Woodlands, Tex. 77380; Stanley J. Gerlich, 11434 Loyola, Cypress, Tex. 77429; Andrew S. Feste, 4219 S. Judson, Houston, Tex. 77005

[21] Appl. No.: 361,295

[22] Filed: Jun. 5, 1989

[51] Int. Cl.⁵ ................... A61K 31/40; A61K 31/195; A61K 31/415
[52] U.S. Cl. .................................... 514/396; 514/419; 514/561
[58] Field of Search ........................ 514/561, 396, 419

[56] References Cited

U.S. PATENT DOCUMENTS

| | | | |
|---|---|---|---|
| 3,697,287 | 10/1972 | Winitz | 514/561 |
| 4,025,650 | 5/1977 | Gans et al. | 514/561 |
| 4,100,160 | 7/1978 | Walser | 514/561 |
| 4,368,204 | 1/1983 | Sato et al. | 514/561 |

OTHER PUBLICATIONS

American Druggist, 10/85, pp. 144–149, "Dickerson".

*Primary Examiner*—Stanley J. Friedman
*Attorney, Agent, or Firm*—John Stanton Schneider

[57] ABSTRACT

An amino acid nutritional supplement and administration regimen for enhancing physical performance through sound nutrition is provided. The amino acid supplement comprises a mixture of biologically active amino acids including at least glutamic acid, arginine, leucine, valine and lysine. The amino acid mixture may also optionally include one or more of histidine, aspartic acid, threonine, serine, proline, glycine, alanine, cystine, methionine, isoleucine, tyrosine, phenylalanine and tryptophan. These amino acid supplements are consumed orally prior to and/or during exercise to achieve the performance enhancement.

34 Claims, No Drawings

AMINO ACID NUTRITIONAL SUPPLEMENT AND REGIMEN FOR ENHANCING PHYSICAL PERFORMANCE THROUGH SOUND NUTRITION

BACKGROUND OF THE INVENTION

The present invention relates generally to compositions of specific nutrients for enhancing physical performance and to the regimens associated with the administration of those particular nutrient compositions. More particularly, the present invention relates to particular combinations of certain biologically active amino acids and their oral administration to accomplish this enhancing of physical performance.

Achieving peak physical performance has long been a goal for self-improvement as well as athletic competitive purposes. The most effective means for improving physical performance involves prolonged systematic exercise and diet training.

Other means, namely pharmaceuticals such as anabolic steroids, are sometimes utilized for enhancing physical performance in conjunction with exercise and diet control. Anabolic steroids are testosterone derivatives which have been reported to promote tissue growth, increase muscle mass, increase hemoglobin concentration and blood volume, improve fatigue recovery and generally improve overall strength and power. For these reasons, anabolic steroids are widely used, often illegally, by numerous persons.

The use of anabolic steroids, however, can result in many serious complications. For example, steroid use has been known to cause interrupted growth and virilization in children, birth defects in the unborn, severe virilization in women, decreased high density lipoprotein levels in blood, disorders of the reproductive system and liver disorders including carcinoma and peliosis hepatis. Steroid use can also result in psychological disorders such as unpredictable mood changes, aggression and libido. Because of these severe side-effects, the use of anabolic steroids is clearly undesirable and has come under considerable attack.

It has now been surprisingly discovered that the controlled oral consumption of effective levels of nutritional mixtures containing certain biologically active amino acids is effective in enhancing physical performance characteristics such as power and intensity of physical exercise as well as endurance of that exercise. By proper administration of the amino acids compositions as detailed below, physical performance can be enhanced through sound nutrition without the deleterious side effects of pharmaceutical performance enhancers.

It is well-known that certain amino acids play a critical nutritional role in muscle development and performance. For example, several investigators have demonstrated that skeletal muscle serves as a major site of branched chain amino acid metabolism. Also, alanine is released from working muscle in large amounts. This alanine is synthesized within the muscle by the transamination of pyruvate and glutamate. The pyruvate is derived from exogenous glucose or muscle glycogen. Once released from the muscle, the newly synthesized alanine is transported to the liver where it is deaminated resulting in the reformation of pyruvate. This constitutes the glucose-alanine cycle which is primarily responsible for transporting toxic ammonia from the working muscle in the form of alanine to be disposed of as urea.

Currently, a number of oral protein supplements, some of which claim to enhance physical performance, are commercially available in the United States. Some include combinations of various amino acids, such as those sold under the trade names MARCOR (a casein supplement sold by Marcor Development Company, Hackensack, N.J.) and UNIPRO (TM) (a "performance enhancer" sold by UNIPRO, Inc., Sunnyvale, Calif.).

The "performance enhancing" supplements are supposed to improve muscle growth, strength, healing, stamina and fat burning, but have not been shown overly effective in enhancing power, intensity, endurance and other indicia of physical performance.

The present invention overcomes the shortcomings of these commercially available supplements by providing a nutritional mixture of certain biologically active amino acids which, when consumed orally, in fact significantly enhances physical performance.

It is, therefore, an object of the present invention to provide nutritional supplements in the form of amino acid compositions, and regimens for oral consumption of these amino acid compositions, which significantly enhance physical performance.

It is a further object of the present invention to provide nutritional supplements in the form of amino acid compositions, and regimens for oral consumption of these amino acid compositions, which do not produce the deleterious side effects which result from the use of anabolic steroid and other pharmaceutical performance enhancers.

SUMMARY OF THE INVENTION

In accordance with the present invention, there are provided nutritional amino acid supplements and regimens for the oral consumption of those amino acid supplements for use in enhancing physical performance. The amino acid supplements and regimens of the present invention are particularly advantageous in that they significantly enhance physical performance through sound nutrition without the deleterious side effects of pharmaceutical performance enhancers.

The amino acid supplements of the present invention comprise, in their overall concept, a mixture of biologically active amino acids, preferable the levorotatory or L-form. More preferably, the supplements comprise a mixture of at least glutamic acid, arginine, leucine, valine and lysine (the "primary" amino acids), optionally also including one or more of histidine, aspartic acid, threonine, serine, proline, glycine, alanine, cystine, methionine, isoleucine, tyrosine, phenylalanine and tryptophan (the "secondary" amino acids). The mixture should comprise between about 40 wt% to 100 wt%, more preferably between about 50 wt% to 100 wt%, still more preferably between about 60 wt% to about 75 wt%, of the primary amino acids Weight percent is based upon the combined weight of the primary and secondary amino acids.

The amino acid supplements of the present invention are preferably consumed orally in the free crystalline form encapsulated in a degradable gelatin capsule or like means. The amino acid supplements may also be consumed as an aqueous solution of the crystalline amino acids. The preferred regimen comprises orally ingesting the amino acid supplement prior to and/or during exercise, more preferably between 15 minutes to one hour prior to exercise, most preferably 30 minutes to 45 minutes prior to exercise, in total dosages ranging from about 0.05 to about 0 5, more preferably from about 0 1 to about 0.4, most preferably about 0.1 to about 0.35, grams of amino acid per kilogram body weight.

The primary advantages of the amino acid supplements and regimens of the present invention over other amino acid supplements and other means of enhancing physical performance include the following: all of the components of the supplement are biologically active nutrient substrates with negligible toxicity or adverse side effects when consumed in the proposed dosage ranges.

These and other features and advantages of the present invention will be more readily understood by those skilled in the art from a reading of the following detailed description and examples.

DETAILED DESCRIPTION OF THE PREFERRED EMBODIMENT

As previously mentioned, the present invention provides amino acids supplements and regimens for orally consuming such amino acids supplements for enhancing physical performance through sound nutrition.

The amino acids supplements of the present invention, in their overall concept, comprise a mixture of biologically active amino acids. These biologically active amino acids exist in a dextrorotatory ("D") and levorotatory ("L") form. The L-form is considerably more biologically active than the D-form and is, therefore, preferred for use in the amino acid supplements of the present invention.

The amino acid supplements of the present invention comprise a mixture of at least five "primary" amino acids: glutamic acid, arginine, leucine, valine and lysine. These amino acids are referred to as "primary" because they are necessarily included in the amino acids supplements of the present invention.

The amino acid supplements of the present invention also preferably include one or more "secondary" amino acids: histidine, aspartic acid, threonine, serine, proline, glycine, alanine, cystine, methionine, isoleucine, tyrosine, phenylalanine and tryptophan. These amino acids are referred to as "secondary" because they are not necessarily, but instead optionally, included in the amino acids supplements of the present invention.

In their overall concept, the amino acid supplements preferably comprise between about 40.0 wt% to about 100 wt%, more preferably between about 50.0 wt% to about 100 wt%, still more preferably between about 60.0 wt% to about 75.0 wt%, of the aforementioned primary amino acids. Conversely, the amino acid supplements preferably comprise between about 0 wt% to about 60.0 wt%, more preferably between about 0 wt% to about 50 0 wt%, still more preferably between about 25 0 wt% to about 40 0 wt%, of the secondary amino acids. In an especially preferred embodiment, as detailed below, the amino acid supplement comprises about 68.5 wt% of the primary amino acids and about 31 5 wt% of the secondary amino acids. The above weight percentages are based upon the combined total weight of the primary and secondary amino acids.

The amino acids are included in the preferred amino acid supplements in the approximate weight percentage ranges as set forth in Table I below. The weight percentage ranges are based upon the total weight of the amino acids in the mixture.

TABLE I

| Amino Acid | More Pref. wt %-wt % | Preferred wt %-wt % |
|---|---|---|
| PRIMARY | | |
| Glutamic Acid | 11.3-27.3 | 10.0-30.0 |
| Arginine | 3.7-6.0 | 3.5-10.0 |
| Leucine | 10.8-13.8 | 10.5-25.0 |
| Valine | 17.2-30.2 | 12.0-40.0 |
| Lysine | 6.5-10.0 | 4.5-12.0 |
| SECONDARY | | |
| Histidine | 1.4-2.0 | 0-3.0 |
| Aspartic Acid | 2.0-6.5 | 0-10.0 |
| Threonine | 1.4-3.3 | 0-5.0 |
| Serine | 1.9-4.1 | 0-5.5 |
| Proline | 4.9-7.6 | 0-10.0 |
| Glycine | 0.8-1.2 | 0-2.0 |
| Alanine | 1.4-1.9 | 0-3.0 |
| Cystine | 0.2-0.5 | 0-1.0 |
| Methionine | 1.2-1.9 | 0-3.0 |
| Isoleucine | 2.5-3.6 | 0-7.5 |
| Tyrosine | 2.2-3.9 | 0-5.5 |
| Phenylalanine | 2.3-3.4 | 0-5.0 |
| Tryptophan | 0.5-0.8 | 0-1.5 |

Note that the secondary amino acids are listed as being optional ingredients in the broad sense of this invention since it is believed that they contribute less to the performance enhancement than the primary amino acids. The secondary amino acids, however, are important from a nutritional point of view and may, in fact, contribute to performance enhancement. Thus, a more preferred amino acid supplement in accordance with the present invention is also set forth above in Table I.

In more preferred formulations, the amino acids are included in the approximate weight percentage ranges as set forth in Table II below. The weight percentage ranges are again based upon the total weight of the amino acids in the mixture.

TABLE II

| Amino Acid | Especially Preferred wt % (±0.05) | Narrow Preferred wt %-wt % |
|---|---|---|
| PRIMARY | | |
| Glutamic Acid | 19.25 | 17.3-21.2 |
| Arginine | 4.85 | 4.3-5.4 |
| Leucine | 12.30 | 11.0-13.6 |
| Valine | 23.70 | 21.3-26.1 |
| Lysine | 8.25 | 7.4-9.1 |
| SECONDARY | | |
| Histidine | 1.65 | 1.4-1.9 |
| Aspartic Acid | 4.25 | 3.8-4.7 |
| Threonine | 2.35 | 2.1-2.6 |
| Serine | 3.00 | 2.7-3.4 |
| Proline | 6.20 | 5.5-6.9 |
| Glycine | 1.00 | 0.8-1.2 |
| Alanine | 1.65 | 1.4-1.9 |
| Cystine | 0.35 | 0.2-0.5 |
| Methionine | 1.60 | 1.4-1.8 |
| Isoleucine | 3.05 | 2.7-3.4 |
| Tyrosine | 3.05 | 2.7-3.4 |
| Phenylalanine | 2.85 | 2.5-3.2 |
| Tryptophan | 0.65 | 0.5-0.8 |

The mixture of amino acids is preferably accomplished by mixing a crystalline form of the amino acid, most preferably the free crystalline form, but also the acetate, chloride and hydrochloride salts may be used. The crystalline form is preferred due to its high purity and the precise, reproducible formations which can be produced from such.

Additionally, the compositions of the present invention may include other essential nutrients such as vitamins, minerals, electrolytes, carbohydrates and the like as required for sound nutrition as will be recognized by one skilled in the art.

As in substantially all biological applications, however, the most preferred nutritional compositions will be patient specific, that is, the actual amino acid mixture may be varied based upon a number of factors which normally determine nutritional compositions such as, for example, the reaction of the specific individual to the composition; the tolerance of the specific individual to the particular and combined components; the age, sex and general condition of the individual; and a number of other factors as will be appreciated by those skilled in the art.

These factors are all related to the ability of a person to utilize or tolerate the amino acid mixture and other components of the nutritional supplements of the present invention. In other words, each patient may require more or less of a specific ingredient depending upon one or more of the above-listed factors. One skilled in the art will be able to recognize these special needs and be able to adjust the compositions of the present invention accordingly.

Other adjustments to the amino acid mixture may be determined from blood and urine amino acid profiles. These profiles are indicative of how the body is utilizing a specific amino acid, and any nutritional deficiency or excess can be determined from such profiles and compensated for by altering the amino acid mixture. One skilled in the art will be able to make the desired adjustments accordingly once such an amino acid profile has been determined.

The regimen comprises orally ingesting the amino acid supplement, prior to and/or during physical activity, in an amount effective to result in physical performance enhancement through sound nutrition. More preferably, the total oral amino acid dosage should range from about 0.05 to about 0.5, still more preferably from 0.1 to about 0.4, most preferably from about 0.1 to about 0 35, grams of amino acid per kilogram body weight.

This total amount may be consumed all at once or may be divided and consumed in smaller amounts prior to and during the physical activity. More preferably, the amino acid supplement is ingested as a single amount from about 15 minutes to about one hour, most preferably from about 30 minutes to about 45 minutes, prior to physical activity.

The nutritional supplements may be administered in any well-known form suitable for oral consumption, but preferably are consumed in the crystalline form encapsulated in a degradable gelatin capsule or other well-known like means.

The amino acid supplements may also be consumed as an aqueous solution of the crystalline amino acids. In a specific example, the amino acid supplement may be added to about eight ounces of water then the solution ingested. Although not all of the amino acid components may dissolve into solution, the entire mixture in this way easily passed into the digestive system for subsequent absorption.

The capsules, aqueous solutions and other forms are compounded using established techniques well known to those skilled in the art to insure the formulation of the ingredients while maintaining the stability, sterility, safety and preferred formulation for the individual.

When so consumed, the amino acid supplements of the present invention result in substantial enhancement of overall physical performance during such physical activity through sound nutrition. The effect is particularly realized under prolonged strenuous activity.

The foregoing detailed discussion of this invention will be further exemplified by the following specific examples offered by way of illustration and not limitation of the above described invention.

EXAMPLES

EXAMPLE 1

In the following example, seven adult males in peak physical condition, achieved mainly by weight lifting and diet control, were tested to determine the effectiveness of the amino acid nutritional supplement as set forth in Table II ("Especially Preferred"), E.P., as compared to a base nutritional supplement sold under the tradename AMINO 1000 by UNIPRO, Inc., of Sunnyvale, Calif. The composition of the AMINO 1000 supplement is reported to be as set forth below in Table III.

TABLE III

| Amino Acid | wt % |
| --- | --- |
| Glutamic Acid | 20.8 |
| Arginine | 3.5 |
| Leucine | 9.3 |
| Valine | 6.5 |
| Lysine | 13.4 |
| Histidine | 2.7 |
| Aspartic Acid | 6.7 |
| Threonine | 3.7 |
| Serine | 4.8 |
| Proline | 9.9 |
| Glycine | 1.9 |
| Alanine | 3.1 |
| Cystine | 0.8 |
| Methionine | 2.9 |
| Isoleucine | 5.3 |
| Tyrosine | 1.4 |
| Phenylalanine | 2.0 |
| Tryptophan | 1.2 |

Four days prior to testing, the subjects stopped taking any daily supplements and began taking a randomly assigned supplement (either AMINO 1000 or the EP formula) as they continued their daily workouts. The supplement used at this stage was consumed in the form of a gelatin capsule to disguise the taste. During the three days prior to testing, the subjects ingested fifteen (15) grams of the particular supplement per day. During the twenty-four (24) hour period prior to testing, the subjects followed their usual meal patterns and did not take any supplement, drink alcohol or work out. On the day of testing, the subjects did not eat for four hours prior to testing but took thirty (30) grams of supplement powder dissolved in 300 cc of aspartame flavored Koolaid(TM) thirty (30) minutes prior to testing. The subjects then remained sedentary prior to exercise. During the testing, the subjects were allowed to sip water ad libidum to prevent dehydration. This was repeated for the alternate supplement one week later.

An exercise protocol was established involving alternating knee extensions and flexions using an OMNI-TRON. The resistance on the OMNI-TRON was set to either #8 or #9 to allow a complete range of motion so multiple repetitions could be performed. The V02 Max was 70–80% indicating exercise of high intensity. The apparatus was calibrated prior to each use by the manufacturer's specifications.

Warm-up: the subjects began the test protocol with a warm up involving twenty (20) minutes of peddling a stationary bicycle at a fixed speed and tension.

Phase I: the subjects began extension followed by flexion in a forceful but nonexhausting manner. After seven consecutive extensions and flexions (one cycle), the subjects rested for forty-five (45) seconds. This routine was then repeated until thirty-five (35) cycles were completed. Power output was recorded for each extension and flexion. The totals are presented in Table IV below.

Interval: the subjects kept warm on the stationary bicycle with the exercise maintained at the same speed and tension used in the warm-up.

Phase II: the subjects then resumed extensions and flexions with ten (10) repetitions (one cycle), followed by a forty-five (45) second rest. These cycles were repeated consecutively until exhaustion. Phase II was terminated after the subject completed the last full cycle of repetitions. The number of cycles to exhaustion and total power for Phase II is presented below in Table IV.

TABLE IV

| Subject | Weight (kg) | Power Phase I UP | Power Phase I EP | Power Phase II UP | Power Phase II EP | Cycles Phase II UP | Cycles Phase II EP |
|---|---|---|---|---|---|---|---|
| A | 105.1 | 85722 | 91666 | 23653 | 78464 | 7 | 25 |
| B | 104.5 | 78569 | 86463 | 19596 | 34910 | 17 | 20 |
| C | 92.7 | 76027 | 86203 | 49949 | 106474 | 20 | 35 |
| D | 82.4 | 75676 | 85484 | 91288 | 129531 | 25 | 34 |
| E | 87.3 | 72864 | 89258 | 34698 | 131275 | 10 | 35 |
| F | 94.1 | 72864 | 89772 | 31472 | 31838 | 12 | 11 |
| G | 90.5 | 72909 | 88275 | 66508 | 96073 | 26 | 35 |
| AVG |  | 76376 | 88160 | 45309 | 86938 | 17 | 28 |

From these results it is clear that the amino acid supplements in accordance with the present invention not only improved strength but also improved endurance. During Phase I of the testing, the use of the present supplements resulted in higher power for each subject. In Phase II, the use of the present supplements not only significantly increased power but also significantly increased the number of additional repetitions that the subjects were able to complete, i.e., significantly increased endurance.

It should be noted that many modifications and variations besides the embodiments specifically mentioned may be made in the aforedescribed nutritional compositions without departing substantially from the concept of the present invention. Accordingly, it should be clearly understood that the form of the invention described and illustrated herein is exemplary only and is not intended as a limitation upon the scope thereof.

We claim:

1. An amino acid nutritional supplement for use in enhancing physical performance through sound nutrition, comprising a mixture of biologically active amino acids comprising:
   from about 10.0 wt% to about 30.0 wt% glutamic acid;
   from about 3.5 wt% to about 10.0 wt% arginine;
   from about 10.5 wt% to about 25.0 wt% leucine;
   from about 12.0 wt% to about 40.0 wt% valine; and
   from about 4.5 wt% to about 12.0 wt% lysine,
wherein said wt% is based upon the total weight of said biologically active amino acids in said mixture.

2. The amino acid supplement of claim 1, wherein said mixture of biologically active amino acids further comprises one or more of histidine, aspartic acid, threonine, serine, proline, glycine, alanine, cystine, methionine, isoleucine, tyrosine, phenylalanine and tryptophan.

3. The amino acid supplement of claim 2, wherein glutamic acid, arginine, leucine, valine and lysine in combination comprise from about 40 wt% to 100 wt% of said mixture.

4. The amino acid supplement of claim 3, wherein glutamic acid, arginine, leucine, valine and lysine in combination comprise from about 50 wt% to 100 wt% of said mixture.

5. The amino acid supplement of claim 4, wherein glutamic acid, arginine, leucine, valine and lysine in combination comprise from about 60 wt% to about 75 wt% of said mixture.

6. The amino acid supplement of claim 1, wherein said mixture of biologically active amino acids further comprises:
   from about 11.3 wt% to about 27.3 wt% glutamic acid;
   from about 3.7 wt% to about 6.0 wt% arginine;
   from about 10.8 wt% to about 13.8 wt% leucine;
   from about 17.2 wt% to about 30.2 wt% valine; and
   from about 6.5 wt% to about 10.0 wt% lysine.

7. The amino acid supplement of claim 6, wherein said mixture of biologically active amino acids further comprises:
   from about 17.3 wt% to about 21.2 wt% glutamic acid;
   from about 4.3 wt% to about 5.4 wt% arginine;
   from about 11.0 wt% to about 13 6 wt% leucine;
   from about 21.3 wt% to about 26.1 wt% valine; and
   from about 7.4 wt% to about 9.1 wt% lysine.

8. The amino acid supplement of claim 7, wherein said mixture of biologically active amino acids further comprises (±0.05 wt%):
   about 19.25 wt% glutamic acid;
   about 4.85 wt% arginine;
   about 12.30 wt% leucine;
   about 23.70 wt% valine; and
   about 8.25 wt% lysine.

9. The amino acid supplement of claim 2, wherein said mixture of biologically active amino acids further comprises:
   from 0 wt% to about 3.0 wt% histidine;
   from 0 wt% to about 10.0 wt% aspartic acid;
   from 0 wt% to about 5.0 wt% threonine;
   from 0 wt% to about 5.5 wt% serine;
   from 0 wt% to about 10.0 wt% proline;
   from 0 wt% to about 2.0 wt% glycine;
   from 0 wt% to about 3.0 wt% alanine;
   from 0 wt% to about 1.0 wt% cystine;
   from 0 wt% to about 3.0 wt% methionine;
   from 0 wt% to about 7.5 wt% isoleucine;
   from 0 wt% to about 5.5 wt% tyrosine;
   from 0 wt% to about 5.0 wt% phenylalanine; and
   from 0 wt% to about 1.5 wt% tryptophan.

10. The amino acid supplement of claim 9, wherein said mixture of biologically active amino acids further comprises:
   from 1 4 wt% to about 2.0 wt% histidine;
   from 2.0 wt% to about 6.5 wt% aspartic acid;
   from 1.4 wt% to about 3.3 wt% threonine;
   from 1.9 wt% to about 4.1 wt% serine;
   from 4.9 wt% to about 7.6 wt% proline;
   from 0.8 wt% to about 1.2 wt% glycine;
   from 1.4 wt% to about 1.9 wt% alanine;

from 0.2 wt% to about 0.5 wt% cystine;
from 1.2 wt% to about 1.9 wt% methionine;
from 2.5 wt% to about 3.6 wt% isoleucine;
from 2.2 wt% to about 3.9 wt% tyrosine;
from 2.3 wt% to about 3.4 wt% phenylalanine; and
from 0.5 wt% to about 0.8 wt% tryptophan.

11. The amino acid supplement of claim 10, wherein said mixture of biologically active amino acids further comprises:
from about 1.4 wt% to about 1.9 wt% histidine;
from about 3.8 wt% to about 4.7 wt% aspartic acid;
from about 2.1 wt% to about 2.6 wt% threonine;
from about 2.7 wt% to about 3.4 wt% serine;
from about 5.5 wt% to about 6.9 wt% proline;
from about 0.8 wt% to about 1.2 wt% glycine;
from about 1.4 wt% to about 1.9 wt% alanine;
from about 0.2 wt% to about 0.5 wt% cystine;
from about 1.4 wt% to about 1.8 wt% methionine;
from about 2.7 wt% to about 3.4 wt% isoleucine;
from about 2.7 wt% to about 3.4 wt% tyrosine;
from about 2.5 wt% to about 3.2 wt% phenylalanine; and
from about 0.5 wt% to about 0.8 wt% tryptophan 12. The amino acid supplement of claim 11, wherein said mixture of biologically active amino acids further comprises ($\pm 0.5$ wt%):
about 1.65 wt% histidine;
about 4.25 wt% aspartic acid;
about 2.35 wt% threonine;
about 3.00 wt% serine;
about 6.20 wt% proline;
about 1.00 wt% glycine;
about 1.65 wt% alanine;
about 0.35 wt% cystine;
about 1.60 wt% methionine;
about 3.05 wt% isoleucine;
about 3.05 wt% tyrosine;
about 2.85 wt% phenylalanine; and
about 0.65 wt% tryptophan.

13. The amino acid supplement of claim 1, wherein said amino acids comprise their levorotatory form.

14. The amino acid supplement of claim 1, wherein said amino acids comprise their free crystalline form.

15. The amino acid supplement of claim 1, wherein said mixture of biologically active amino acids is encapsulated for oral administration.

16. A nutritional method for enhancing physical performance, comprising the step of orally consuming an effective amount of an amino acid supplement prior to and/or during exercise, said amino acid supplement comprising a mixture of biologically active amino acids comprising:
from about 10.0 wt% to about 30.0 wt% glutamic acid;
from about 3.5 wt% to about 10.0 wt% arginine;
from about 10.5 wt% to about 25.0 wt% leucine;
from about 12.0 wt% to about 40.0 wt% valine; and
from about 4.5 wt% to about 12.0 wt% lysine,
wherein said wt% is based upon the total weight of said biologically active amino acids in said mixture.

17. The method of claim 16, wherein said mixture of biologically active amino acids further comprises one or more of histidine, aspartic acid, threonine, serine, proline, glycine, alanine, cystine, methionine, isoleucine, tyrosine, phenylalanine and tryptophan.

18. The method of claim 17, wherein glutamic acid, arginine, leucine, valine and lysine in combination comprise from about 40 wt% to 100 wt% of said mixture.

19. The method of claim 18, wherein glutamic acid, arginine, leucine, valine and lysine in combination comprise from about 50 wt% to 100 wt% of said mixture.

20. The method of claim 19, wherein glutamic acid, arginine, leucine, valine and lysine in combination comprise from about 60 wt% to about 75 wt% of said mixture.

21. The method of claim 16, wherein said mixture of biologically active amino acids further comprises:
from about 11.3 wt% to about 27.3 wt% glutamic acid;
from about 3.7 wt% to about 6.0 wt% arginine;
from about 10.8 wt% to about 13.8 wt% leucine;
from about 17.2 wt% to about 30.2 wt% valine; and
from about 6.5 wt% to about 10.0 wt% lysine.

22. The method of claim 21, wherein said mixture of biologically active amino acids further comprises:
from about 17.3 wt% to about 21.2 wt% glutamic acid;
from about 4.3 wt% to about 5.4 wt% arginine;
from about 11.0 wt% to about 13.6 wt% leucine;
from about 21.3 wt% to about 26.1 wt% valine; and
from about 7.4 wt% to about 9.1 wt% lysine 23. The method of claim 22, wherein said mixture of biologically active amino acids further comprises ($\pm 0.05$ wt%):
about 19.25 wt% glutamic acid;
about 4.85 wt% arginine;
about 12.30 wt% leucine;
about 23.70 wt% valine; and
about 8.25 wt% lysine 24. The method of claim 17, wherein said mixture of biologically active amino acids further comprises:
from 0 wt% to about 3.0 wt% histidine;
from 0 wt% to about 10.0 wt% aspartic acid;
from 0 wt% to about 5.0 wt% threonine;
from 0 wt% to about 5.5 wt% serine;
from 0 wt% to about 10.0 wt% proline;
from 0 wt% to about 2.0 wt% glycine;
from 0 wt% to about 3.0 wt% alanine;
from 0 wt% to about 1.0 wt% cystine;
from 0 wt% to about 3.0 wt% methionine;
from 0 wt% to about 7.5 wt% isoleucine;
from 0 wt% to about 5.5 wt% tyrosine;
from 0 wt% to about 5.0 wt% phenylalanine; and
from 0 wt% to about 1.5 wt% tryptophan.

25. The method of claim 24, wherein said mixture of biologically active amino acids further comprises:
from 1.4 wt% to about 2.0 wt% histidine;
from 2.0 wt% to about 6.5 wt% aspartic acid;
from 1.4 wt% to about 3.3 wt% threonine.,
from 1.9 wt% to about 4.1 wt% serine;
from 4.9 wt% to about 7.6 wt% proline;
from 0.8 wt% to about 1.2 wt% glycine;
from 1.4 wt% to about 1.9 wt% alanine;
from 0.2 wt% to about 0.5 wt% cystine;
from 1.2 wt% to about 1.9 wt% methionine;
from 2.5 wt% to about 3.6 wt% isoleucine;
from 2.2 wt% to about 3.9 wt% tyrosine;
from 2.3 wt% to about 3.4 wt% phenylalanine; and
from 0.5 wt% to about 0.8 wt% tryptophan 26. The method of claim 25, wherein said mixture of biologically active amino acids further comprises:
from about 1.4 wt% to about 1.9 wt% histidine;
from about 3.8 wt% to about 4.7 wt% aspartic acid;
from about 2.1 wt% to about 2.6 wt% threonine;
from about 2.7 wt% to about 3 4 wt% serine;
from about 5.5 wt% to about 6.9 wt% proline;

from about 0.8 wt% to about 1.2 wt% glycine;
from about 1.4 wt% to about 1.9 wt% alanine;
from about 0.2 wt% to about 0.5 wt% cystine;
from about 1.4 wt% to about 1.8 wt% methionine;
from about 2.7 wt% to about 3.4 wt% isoleucine;
from about 2.7 wt% to about 3.4 wt% tyrosine;
from about 2.5 wt% to about 3.2 wt% phenylalanine; and
from about 0.5 wt% to about 0.8 wt% tryptophan.

27. The method of claim 26, wherein said mixture of biologically active amino acids further comprises (±0 05 wt%):
about 1.65 wt% histidine;
about 4.25 wt% aspartic acid;
about 2.35 wt% threonine;
about 3.00 wt% serine;
about 6.20 wt% proline;
about 1.00 wt% glycine;
about 1.65 wt% alanine;
about 0.35 wt% cystine;
about 1.60 wt% methionine;
about 3.05 wt% isoleucine;
about 3.05 wt% tyrosine;
about 2.85 wt% phenylalanine; and
about 0.65 wt% tryptophan.

28. The method of claim 16, wherein said amino acids comprise their levorotatory form.

29. The method of claim 16, wherein said amino acids comprise their free crystalline form.

30. The method of claim 16, wherein said amino acid supplement is orally consumed in a total amount of about 0.05 to about 0.5 grams of amino acid per kilogram body weight.

31. The method of claim 30, wherein said amino acid supplement is orally consumed in a total amount of about 0.1 to about 0.4 grams of amino acid per kilogram body weight.

32. The method of claim 31, wherein said amino acid supplement is orally consumed in a total amount of about 0.1 to about 0.35 grams of amino acid per kilogram body weight.

33. The method of claim 16, wherein said amino acid supplement is orally consumed as a single amount from about 15 minutes to about one hour prior to exercise.

34. The method of claim 33, wherein said amino acid supplement is orally consumed as a single amount from about 30 minutes to about 45 minutes prior to exercise.

* * * * *